United States Patent
Feller et al.

(10) Patent No.: US 9,797,873 B1
(45) Date of Patent: Oct. 24, 2017

(54) PREDICTION OF RECIPE PREPARATION TIME

(71) Applicant: Yummly, Inc., Redwood City, CA (US)

(72) Inventors: David B. Feller, Mountain View, CA (US); Vadim Geshel, Redwood City, CA (US); Gregory Allen Druck, Jr., San Francisco, CA (US); Ryan N. Smith, Burlingame, CA (US)

(73) Assignee: Yummly, Inc., Redwood City, CA (US)

( * ) Notice: Subject to any disclaimer, the term of this patent is extended or adjusted under 35 U.S.C. 154(b) by 565 days.

(21) Appl. No.: 14/316,060

(22) Filed: Jun. 26, 2014

(51) Int. Cl.
    *G01N 33/00* (2006.01)

(52) U.S. Cl.
    CPC .................. *G01N 33/00* (2013.01)

(58) Field of Classification Search
    CPC .... G01N 33/00; G06Q 30/02; G06Q 30/0282; G06Q 30/0621
    USPC ........................................................ 702/176
    See application file for complete search history.

(56) References Cited

U.S. PATENT DOCUMENTS

2011/0055044 A1* 3/2011 Wiedl .................... G06Q 30/02
                                                        705/26.5
2014/0280148 A1  9/2014 Stankiewicz

OTHER PUBLICATIONS

"The Stanford Parser: A Statistical Parser," The Stanford Natural Language Processing Group, 4 pages, Version Release Aug. 27, 2014 [Online] [Retrieved on Sep. 11, 2014] Retrieved from the Internet<URL:http://nlp.stanford.edu/software/lex-parser.shtml.
De Marneffe, M.-C. et al., "Generating Typed Dependency Parses from Phrase Structure Parses," In LREC 2006, 2006, pp. 449-454.
Klein, D. et al., "Accurate Unlexicalized Parsing," Proceedings of the 41st Meeting of the Association for Computational Linguistics, 2003, pp. 423-430.
Klein, D. et al., "Fast Exact Inference with a Factored Model for Natural Language Parsing," In Advances in Neural Information Processing Systems 15 (NIPS 2002), Cambridge, MA: MIT Press, 2003, pp. 3-10.
Socher, R. et al., "Parsing With Compositional Vector Grammars," Proceedings of $51^{st}$ Annual Meeting of the Association for Computational Linguistics, Aug. 4-9, 2013, pp. 455-465.

* cited by examiner

Primary Examiner — Bryan Bui
(74) Attorney, Agent, or Firm — Fenwick & West LLP (57) ABSTRACT

Embodiments infer a total preparation time of a recipe. A recipe including preparation steps describing how to prepare a food item is obtained. A recipe server identifies preparation features in the preparation steps, where the preparation features represent portions of the preparations steps that are correlated with time to prepare the recipe. The recipe server obtains preparation times associated with the preparation features and combines these preparation times to estimate to total preparation time of the recipe. The estimated total preparation time is stored or transmitted to a client device in response to a request for the recipe. The estimated total preparation time is used to filter recipes sent in response to a request for recipes, where the request specifies a criterion based on total preparation time. The estimated total preparation time is used to select recipes for recommendation to a user based on that user's preferences.

15 Claims, 6 Drawing Sheets

Mr. Sam's Kitchen

Tater Stew　─513
Serves 3, 150 minutes

Ingredients:　─520

1 gallon water
2 carrots and turnips
3 bay leaves
6 Russet potatoes
18 oz. rabbit
thyme and sage, to taste Directions:

Cut rabbit into cubes and cook to medium ─530A
530B─　　over open flame.
　　　Wash and dice Russet potatoes, carrots,
　　　　and turnips.　　─530C
　　　Add bay leaves, thyme, and sage to water
530D─　　before boiling.
　　　Stew rabbit, potatoes, carrots, and turnips
　　　　for two hours.

PREDICTION OF RECIPE PREPARATION TIME

BACKGROUND

Field of Disclosure

This disclosure relates generally to natural language processing and more particularly to inferring time to prepare a food item described in a recipe.

Description of the Related Art

Although recipes are available from many sources (e.g., the Internet), such recipes do not have a standard format and may omit useful information about the recipe such as the total time to prepare a food item described in the recipe. Additionally, some recipes may include inaccurate preparation times because preparation times vary with the skill of the cook. A skilled cook may indicate a total preparation time for a recipe that is much lower than the time an average recipe reader would spend to prepare the food item.

When curating an information source including a large number of recipes, it is infeasible to determine the preparation time of every recipe experimentally. Some food preparation times (e.g., time to cook a turkey in an oven) may be determined mathematically (e.g., a heat transfer analysis of a turkey in an oven). Recipes contain other preparation steps, however, whose time does not follow a mathematical relationship, so it is not practical to estimate a recipe's preparation time a priori. Additionally, the large number of possible combinations of ingredients, cooking techniques, and cooking equipment precludes empirically determining preparation times for each combination. Thus, present techniques are ill-suited for estimating total preparation times for a large number of recipes.

SUMMARY

Embodiments infer a total preparation time for a recipe. A recipe that includes preparation steps is obtained. The preparation steps describe how to prepare a food item described by the recipe. Preparation features in the preparation steps are identified. These preparation features represent portions of the preparation steps that are indicative of time to prepare the recipe. Preparation times that are associated with the preparation features are obtained, and the total preparation time of the recipe is estimated by combining the preparation times that are associated with the identified preparation features. For example, the preparation times (or a subset thereof) are summed to estimate the total preparation time.

The estimated total preparation time is stored or transmitted to a client device in response to a request for the recipe from the client device. In one embodiment, a request for recipes within a threshold total preparation time is received from a client device. The recipe is transmitted to the client device in response to determining that the total preparation time of the recipe is within the threshold preparation time. In one embodiment, recipe preparation times are estimated for multiple recipes. A subset of these recipes are selected for recommendation to the user based on the total preparation times and user preferences of the user.

In one embodiment, the obtained preparation times associated with preparation steps are determined using a preparation time model. Training preparation features are identified in training recipes having known total preparation times, and the preparation time model is trained to predict the total preparation times from the identified training preparation features. The predicted total preparation time is compared to the known total preparation time of the training recipes to refine the preparation time model. In one embodiment, the preparation time model is a linear regression between the training preparation features and the known total preparation times.

Embodiments include methods of inferring or estimating a total preparation time of a recipe from preparation steps of that recipe. Embodiments of the computer-readable storage medium store computer-executable instructions for performing the steps described above. Embodiments of the system further comprise a processor for executing the computer-executable instructions.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

The Figures (FIGS.) and the following description describe certain embodiments by way of illustration only. One skilled in the art will readily recognize from the following description that alternative embodiments of the structures and methods illustrated herein may be employed without departing from the principles described herein.

DETAILED DESCRIPTION

Reference will now be made in detail to several embodiments, examples of which are illustrated in the accompanying figures. It is noted that wherever practicable similar or like reference numbers may be used in the figures and may indicate similar or like functionality.

Recipe Extraction Environment

Figure 1:
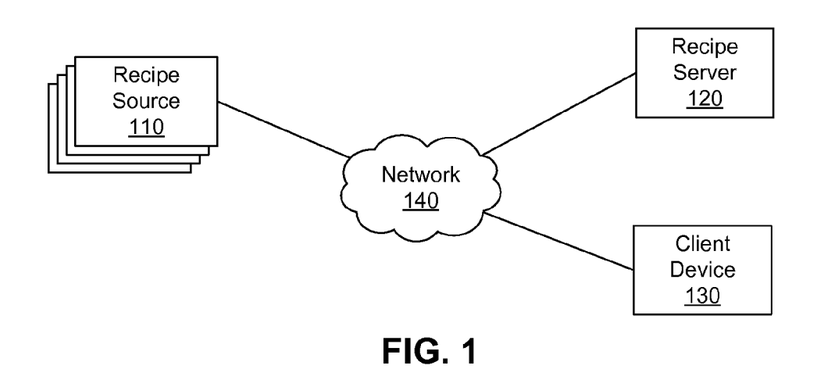
FIG. 1 is a high-level block diagram illustrating an environment for estimating total preparation times of recipes, in accordance with an embodiment.

FIG. 1 is a high-level block diagram illustrating an environment 100 for estimating total preparation times of recipes, in accordance with an embodiment. The environment 100 includes entities such as recipe sources 110, a recipe server 120, a client device 130, and a network 140. Although single instances of some of the entities are illustrated, multiple instances may be present. For example, multiple client devices 130 associated with multiple users may access recipes through the recipe server 120. The functionalities of the entities may be distributed among multiple instances. For example, a content distribution network (or a cloud-based network) of servers at geographically dispersed locations implements the recipe server 120 to increase server responsiveness.

A recipe source 110 is a repository of recipes accessible by the recipe server 120. Recipes are media describing preparation of a food item through text, images, video, animations, or other media. A food item is typically an edible substance consumed for nutrition or gustatory sensation and includes both solid and non-solid food items (e.g., beverages). In one embodiment, the recipe source 110 is a server hosting a webpage displaying recipes through a markup language (e.g., HTML) or another structured document format. A recipe source 110 may implement an application programming interface (API) functionality to provide recipe access to applications native to an operating system on a client device 130. The recipe source 110 may be implemented using a server, described further with respect to FIG. 7.

Alternatively or additionally, a recipe source 110 is a repository containing recipes in a structured document format. The repository may be a non-transitory computer-readable storage medium (e.g., a hard disk drive, an optical disc, a flash memory) accessible to the recipe server through the network 140 or through a removable storage media interface. Non-transitory computer-readable storage media are further described with respect to FIG. 7.

The recipe server 120 hosts recipes for display to the user of a client device 130. In one embodiment, the recipe server 120 retrieves recipes from a recipe source 110 and analyzes the recipes to enable more uniform presentation through client devices 130 and to enable more efficient organization of recipes. The recipe server 120 may also infer properties of recipes such as preparation time of a recipe, expected number of servings, difficulty of a recipe, and necessary cooking techniques or equipment. The recipe server 120 may also infer properties of food items described in recipes (e.g., nutrition, flavor) as well as culinary groupings of the food item by tradition (e.g., cuisine), by time (e.g., typical meal, related holidays) or by pairings with other food (e.g., typical course within a meal). Optionally, the recipe server 120 organizes recipes to present relevant or recommended recipes to a user of a client device 130. For example, the recipe server 120 organizes recipes to accurately interpret search queries better than a generic search algorithm. As another example, the recipe server 120 maintains a user profile to log a user's preferences, dietary restrictions, and culinary tastes. This user profile may be used to recommend items to the user and to increase relevance of search results to the user. The recipe server 120 is described further with respect to FIG. 2.

The client device 130 accesses recipes through the network 140 and presents the accessed recipes to the user. In one embodiment, the client device 130 is a computer, which is described further below with respect to FIG. 7. Example client devices 130 include a desktop, a laptop, a tablet, a mobile device, a smart television, and a wearable device. Using the client device 130, a user may access recipes on the recipe server 120. Optionally, the user of a client device 130 may search through recipes on the recipe server 120 or request recipe recommendations from the recipe server 120. The client device 130 may contain software such as a web browser or another application for viewing recipes from the recipe server 120. The client device 130 may optionally access a recipe source 110 that displays recipes through a webpage or in another accessible form through the network 140.

The network 140 enables communications among the entities connected to it through one or more local-area networks and/or wide-area networks. In one embodiment, the network 140 is the Internet and uses standard wired and/or wireless communications technologies and/or protocols. The network 140 can include links using technologies such as Ethernet, 802.11, worldwide interoperability for microwave access (WiMAX), long term evolution (LTE), 3G, 4G, digital subscriber line (DSL), asynchronous transfer mode (ATM), InfiniBand, and/or PCI Express Advanced Switching. Similarly, the networking protocols used on the network 140 can include multiprotocol label switching (MPLS), transmission control protocol/Internet protocol (TCP/IP), User Datagram Protocol (UDP), hypertext transport protocol (HTTP), simple mail transfer protocol (SMTP), and/or file transfer protocol (FTP). The network 140 may include multiple sub-networks linked to transfer data.

The data exchanged over the network 140 can be represented using technologies and/or formats including hypertext markup language (HTML), extensible markup language (XML), and/or JavaScript Object Notation (JSON). In addition, all or some of the transmitted data can be encrypted using conventional encryption technologies such as the secure sockets layer (SSL), transport layer security (TLS), virtual private networks (VPNs), and/or Internet Protocol security (IPsec). In another embodiment, the entities use custom and/or dedicated data communications technologies instead of, or in addition to, the ones described above.

Recipe Server

Figure 2:
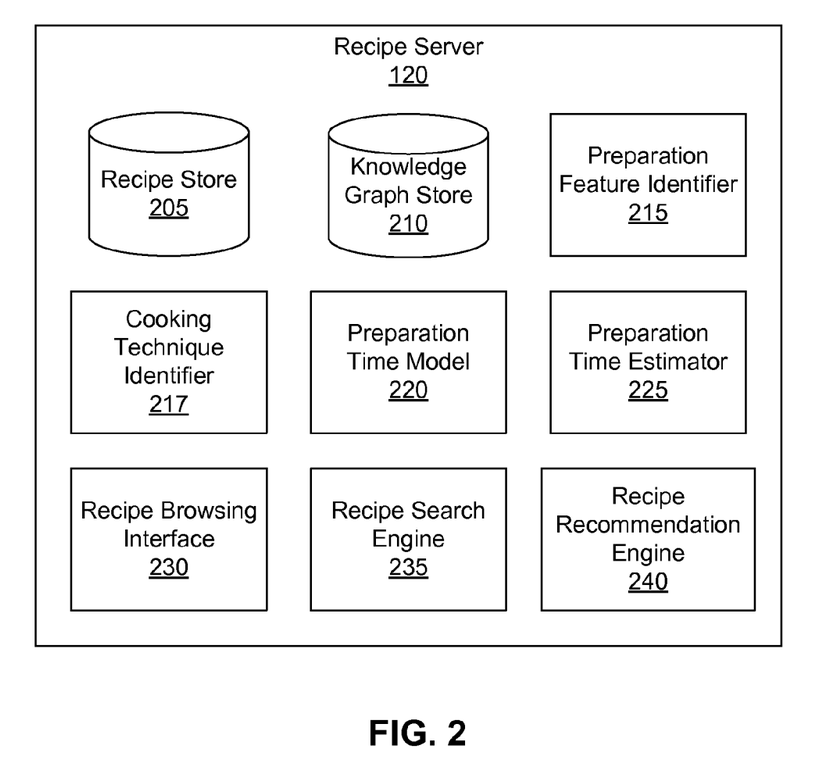
FIG. 2 is a block diagram illustrating a recipe server, in accordance with an embodiment.

FIG. 2 is a block diagram illustrating a recipe server 120, in accordance with an embodiment. The recipe server 120 includes a recipe store 205, a knowledge graph store 210, a preparation feature identifier 215, a cooking technique identifier 220, a preparation time model 217, a preparation time estimator 225, a recipe browsing interface 230, a recipe search engine 235, and a recipe recommendation engine 240.

Recipe and Knowledge Graph Stores

The recipe store 205 contains labeled recipes. A labeled recipe includes source content of a recipe (or a pointer thereto) and classified recipe components. The source content of the recipe may be stored as a copy of the recipe from its original recipe source 110, or a pointer to the recipe on the recipe source 110. The source content of the recipe includes text of the recipe as well as accompanying images or other media (e.g., video, animations). A classified recipe component is content of a recipe that includes a type of information about a recipe such as its ingredients or its preparation steps. Other classified recipe components may include a number of servings, a serving size, a preparation time, or a recipe title, for example.

The recipe server 120 obtains classifications of recipe components for storage in the recipe store 205. The recipe server 120 may obtain labels for recipe components from formatting metadata associated with the recipe and retrieved from the recipe source 110. Example recipe formatting metadata labels the recipe's title, ingredient block, and preparation steps. Alternatively or additionally, the recipe server 120 receives manual classifications of recipe components from a user through an interface to facilitate manual classification. In one embodiment, the recipe server 120 separates the content of a recipe from the recipe source into segments and classifies segments as different recipe components. For example, the recipe server 120 uses a machine learning algorithm (e.g., conditional inference on a random field, logistic regression) to infer recipe component classifications from features of the recipe including its structure and occurrences of known food-related terms (such as those in the knowledge graph 210). Various techniques for classifying recipe components are described in U.S. application Ser. No. 14/284,076, filed May 21, 2014, which is incorporated by reference in its entirety. Thus, the recipe store 205 contains labeled recipes with classified recipe components The knowledge graph store 210 contains a graph representing food knowledge. Example sections of the knowledge graph are provided in FIGS. 6A and 6B. The nodes of the graph represent food-related terms such as ingredients, cooking techniques, cooking equipment, and abstractions of food-related terms. Example nodes of the graph include "apple," "Gala apple," "fruit," "slicing," "peeling," "knife," and "peeler." Abstractions are broader categories of food-related terms, such as ingredients. For example, "steak" is an abstraction of "rib-eye steak." A node may be an abstraction with respect to another node and an ingredient with respect to another node. For example, "beef" is an abstraction of "Wagyu beef," and "meat" is a further abstraction of "beef." A cooking technique is a method of preparing a food item. Example nodes representing cooking techniques include "sautéing," "searing," and "sous vide." A piece of cooking equipment is a device or tool for preparing a food item. Example nodes representing cooking equipment include a "baking stone," a "mushroom brush," and "bamboo skewers." Similar to ingredients, a node representing a cooking technique or a piece of cooking equipment may be an abstraction of a cooking technique or a piece of cooking equipment. For example, nodes representing the cooking techniques "cutting" and "cooking" are abstractions of the cooking techniques "mincing" and "browning," respectively. As another example, a "baking container" is an abstraction of the cooking equipment "muffin pan" and "cookie sheet."

A node of the food knowledge graph may contain attributes of the food-related term that the node represents. For example, nodes representing ingredients contain nutritional density information and associated allergens and dietary restrictions. Nodes representing abstractions may similarly contain average nutritional density information as well as attributes (e.g., allergens such as gluten or nuts, dietary restrictions such as halal, vegan, or kosher) common to child ingredients of a parent abstraction. As another example, nodes representing cooking techniques and cooking equipment indicate difficulty of using cooking equipment or learning a cooking technique.

A node of the food knowledge graph may contain alternative names for a food-related term that the node represents. For instance, a node representing a piece of cooking equipment includes alternative commercial names of the cooking equipment. For example, a node representing a "contact grill" includes "George Foreman™ grill" as an alternative name. A node representing a cooking technique may include different verb conjugations and other word forms of that cooking technique. For example, the node representing the cooking technique "baking" includes the different verb conjugations "bake," "baking," "baked," and "bakes" as alternative names for "baking." Alternatively or additionally, a node includes a pointer to an external dictionary or other database indicating alternative names for a food-related term.

The edges of the food knowledge graph may indicate relationships between nodes of the graph. The food knowledge graph has different types of edges representing different relationships, and two nodes may be connected by more than one edge. For example, one type of edge explicitly indicates the parent-child relationship between an ingredient and an abstraction (e.g., "black beans are a kind of beans"). Another type of edge between two nodes representing two ingredients indicates that the ingredients have equivalent nutritional content (e.g., "a Fuji apple is the nutritional equivalent of a Gala apple"). Edges may connect similar nodes, such as an edge representing substitutability between ingredients represented by two nodes. An edge between a node representing an ingredient and a node representing cooking equipment or a cooking technique indicates that the ingredient is commonly used with the cooking equipment or technique (e.g., "potatoes are often used with ovens," "potatoes are often baked"). Similarly, an edge between a node representing a cooking technique and a node representing cooking equipment indicates that the cooking equipment may be used in a cooking technique (e.g., "an oven is used for baking").

In addition to ingredients, abstractions of ingredients, cooking techniques, and cooking equipment, the knowledge graph may contain nodes representing units of measure (e.g., cup, ounce, cubic centimeter, pinch). These nodes may have attributes indicating common abbreviations of the unit of measure, and edges between these nodes may represent unit conversions between dimensionally consistent units of measure. Hence, the nodes, attributes of nodes, and edges between nodes serve to organize food knowledge in the knowledge graph store 210.

The knowledge graph store 210 may be used by the preparation feature identifier 215 to identify preparation features in preparation steps of a recipe. By combining preparation times associated with these preparation features, the preparation time estimator 225 infers the total preparation time of a recipe. The preparation times associated with preparation features are determined by the preparation time model 220. The recipe server 120 uses the estimated total preparation time in the recipe browsing interface 230, the recipe search engine 235, or the recipe recommendation engine 240.

Preparation Features

The preparation feature identifier 215 generates preparation features from the preparation steps of a recipe. Preparation features are content or attributes of preparation steps that are related to the total preparation time of the recipe. The preparation feature identifier 215 may generate preparation features for each preparation step of a recipe separately or may generate preparation features for multiple preparation steps at a time. The preparation feature identifier 215 may isolate individual preparation steps using punctuation (e.g., periods, semicolons), line breaks, or other formatting (e.g., numbering, bullets).

The preparation feature identifier 215 identifies preparation features from text corresponding to preparation equipment, cooking techniques, ingredients, or other nodes in the knowledge graph store 210. For the example recipe preparation step "mash the potatoes with a potato ricer," the preparation feature identifier 215 creates preparation features corresponding to the cooking technique "mashing," the cooking equipment "potato ricer," and the ingredient "potato." The food knowledge graph may include alternative names for food items, which the preparation feature identifier 215 uses to match text of a preparation step with a node of the food knowledge graph.

The preparation feature identifier 215 may generate features corresponding to two or more nodes of the food knowledge graph present in a preparation step. These preparation features may capture combinations of cooking techniques, ingredients, or cooking equipment that have abnormal preparation times. For example, "bake the turkey" and "bake a salmon" are associated with different preparation times because a whole turkey is typically thicker than a salmon.

Besides preparation features corresponding to nodes of the food knowledge graph, the preparation feature identifier 215 may generate features corresponding to text of a preparation step. A preparation feature may correspond to one or more words of text that modify the average preparation time of a preparation step (e.g., "cook to medium rare" vs. "cook to medium well"). Preparation features corresponding to text account for preparation step modifiers not represented in the food knowledge graph. Modifiers are words or phrases (e.g., "medium well") that affect how long a preparation step takes. For example, "cutting garlic into quarters" takes less time than "cutting garlic into sixteenth-inch pieces." Preparation features representing text such as "into quarters" or "into sixteenth-inch pieces" account for these preparation step modifiers.

The preparation feature identifier 215 may generate preparation features corresponding to explicit times in the preparation steps (e.g., "the rice is boiled for five minutes"). The preparation feature identifier may identify these explicit mentions of time based on text fitting the expression "<number> <unit of time measure>," for example. By accounting for explicit time instructions, these preparation features beneficially improve accuracy of total calculated preparation times.

In one embodiment, the preparation feature identifier 215 uses the cooking technique identifier 217 to recognize cooking techniques. Cooking techniques typically occur as verbs in text, which complicates matching of text to terms in the knowledge graph 210 because of difficulty identifying the main verb of a sentence. Recipes may refer multiple times to a preparation step performed once. For example, the cooking technique is referred to in its gerund form in an explanatory sentence about a preparation step (e.g., "The oven should be preheated to 400° F. prior to baking the salmon."). As another example, a recipe calls for use of a prepared ingredient with a form of a preparation technique in its name (e.g., "top the chilled cream cheese with smoked salmon"). Identifying all of the possible mentions of a cooking technique as separate preparation features would erroneously inflate the estimated total preparation time of the recipe due to duplicate mentions of cooking techniques in the gerund form. Thus, the preparation feature identifier is used to avoid misidentification of cooking techniques, as in "baking," "chilled," and "smoked" from the previous examples.

To ensure that identified preparation features correspond to an actual cooking technique, the preparation feature identifier uses the cooking technique identifier 217. In one embodiment, the cooking technique identifier 217 separates the preparations steps of a recipe into sentences (or clauses of a sentence) and then determines the part of speech for different words in the preparation step. For example, the cooking technique identifier 217 creates a dependency tree reflecting the structure of the sentence and assigns, based on the dependency tree, part-of-speech tags indicating whether a given word is a noun, article, adjective, verb, or other part of speech (e.g., using the Stanford Parser software package). The cooking technique identifier 217 may refer to the food knowledge graph to identify verbs from words matching cooking techniques. In one embodiment, the cooking technique identifier 217 identifies the cooking technique of a preparation step as the verb in the main clause of the preparation step.

In another embodiment, the cooking technique identifier 217 includes statistical classifiers for different cooking techniques. The cooking technique identifier 217 generates input features for the statistical classifiers. Based on these input features, a statistical classifier has an output (e.g., a probability, a binary output) indicating whether a preparation step contains a given cooking technique. The cooking technique identifier 217 may then recognize one or more cooking techniques as present in a preparation step based on the outputs of the statistical classifiers.

The cooking technique identifier 217 generates input features that reflect the content of the preparation steps, the part-of-speech tag determined for a word, or the structure of the dependency tree. Features based on the content of the preparation steps include words matching nodes of the food knowledge graph as well as features matching abstractions of the food knowledge graph. For the example preparation step "boil the rotini," the cooking technique identifier 217 creates features corresponding to the ingredient "rotini," the ingredient abstraction "pasta," and the cooking technique "boiling." Features based on part of speech may account for correlation between a cooking technique and its part of speech. For the previous example preparation step, a feature indicates that the cooking technique "boil" is also the verb of the sentence's main clause. Other features for the statistical classifier are based on the structure of a dependency tree. For example, a feature indicates the distance in the dependency tree between an ingredient and its nearest ancestor node in common with the object of the main clause.

Using the generated features as inputs to the statistical classifiers, the cooking technique identifier 217 identifies one or more cooking techniques associated with a preparation step. To identify a cooking technique, the cooking technique identifier 217 determines the output of the statistical classifiers and selects one or more cooking techniques based on a ranking of the outputs of the statistical classifiers. Alternatively or additionally, the cooking technique identifier 217 selects one or more cooking techniques having outputs (from the corresponding one or more statistical classifiers) above a threshold. To train the statistical classifiers, the cooking technique identifier 217 uses training preparation steps with labeled cooking techniques. The statistical classifiers are then trained (e.g., using logistic regression) so that the output of the classifiers mimics the labeled cooking techniques in the training recipes. Using the identified one or more cooking techniques from the cooking technique identifier 217, the preparation feature identifier 215 creates preparation features for use by the preparation time model 220 and the preparation time estimator 225.

Although the preparation feature identifier 215 and the cooking technique identifier 217 are described as generating preparation features and identifying cooking techniques from text, the identifiers 215 and 217 may alternatively or additionally use images, videos, audio, animations, or other media. For example, the recipe server 120 applies optical character recognition to recognize text in images, videos, or animations to produce text analyzable by the identifiers 215 and 217. As another example, the recipe server 120 uses speech-to-text transcription to recognize spoken text in videos or audio.

Total Preparation Time

The preparation time model 220 determines preparation times associated with preparation features using training recipes. The training recipes include preparation steps and known total preparation times. The known total preparation time may be obtained from the recipe source 110, for example. The feature identifier 215 generates training preparation features from training recipes. These features are input into the preparation time model 220, which determines preparation times associated with the training preparation features such that the preparation time model 220 outputs an estimated total preparation time similar to the known total preparation time of a training recipe.

In one embodiment, the preparation time model 220 uses multiple linear regression between the input training preparation features and the known total preparation times to determine preparation times that are associated with the preparation features. The coefficients determined for the linear regression correspond to the preparation times associated with the training preparation features in the regression. For example, the preparation time model 220 minimizes an objective function such as a measure of error (e.g., sum-squared error) between estimated total preparation times output by the model 220 and corresponding known total preparation times. The determined preparation times are stored in association with the corresponding training preparation features.

In one embodiment, the preparation time model 220 enforces a non-negativity constraint on preparation times. For example, the preparation time model 220 enforces a non-negativity constraint on the coefficients of the linear regression. This constraint ensures that preparation features are not associated with negative preparation times.

Alternatively, the preparation time model 220 allows negative preparation times, which reflect that some preparation features correspond to reduced total preparation times. For example, the text "meanwhile" indicates that a preparation step is carried out in parallel with another preparation step, reducing the total preparation time compared to doing them serially. An example preparation feature representing the text "meanwhile" is associated with negative preparation times to reflect the reduced total preparation time from parallelization. Other example preparation features representing the cooking equipment "microwave" and the text "optionally" are both associated with negative preparation times.

Optionally, the preparation time model 220 may include a regularizer term in its objective function (e.g., in addition to an error term) to avoid over-fitting of data. For example, a L1 regularizer adds the sum of the determined preparation times' magnitudes (i.e., the L1 norm, or taxicab distance of a vector of the preparation times from the origin) to the objective function. Performing L1 regularization (or some other regularization) may result in some training preparation features receiving an associated preparation time of zero (or a substantially negligible preparation time). Such preparation features having an associated preparation time of zero (or a preparation time below a threshold) may be omitted from the preparation time model 220, which beneficially reduces computational time to subsequently estimate total recipe preparation times.

In one embodiment, the preparation time model 220 determines preparation time associated with training preparation features for some training preparation features through a linear regression but determines preparation times associated with other training preparation features through different means. For example, if a training preparation feature corresponds to an explicit preparation time, then the preparation time model 220 associates that training preparation feature with a preparation time equal to the identified explicit preparation time. In this example, the preparation time model 220 may furthermore remove from the regression preparation features generated from the same preparation step as the preparation feature indicating an explicit time. By removing from the regression those preparation features besides the preparation feature corresponding to an explicit preparation time, the preparation time model 220 prevents duplicate time contributions from the same preparation step.

Using preparation features for a recipe generated by the preparation feature identifier 215 from preparation steps of a recipe, the preparation time estimator 225 infers a total preparation time. The preparation time estimator 225 obtains preparation times associated with the preparation features and combines these preparation times to estimate the total preparation time of the recipe. The preparation times may be determined using the preparation time model 220. Alternatively or additionally, preparation times are derived for preparation features based on deductive rules (e.g., estimating cooking time using a heat transfer equation) or empirical data. The preparation times are typically retrieved from storage to decrease computational time, but the preparation times may also be computed substantially in real time (e.g., by the preparation time model 220 in response to a request for a total preparation time).

In one embodiment, a preparation time corresponding to a preparation feature is modified based on a quantity of an ingredient involved in that preparation feature. The recipe model 220 may determine a relationship (e.g., using a linear regression) between a quantity of an ingredient and the preparation time associated with a preparation feature corresponding to that ingredient. The preparation time estimator 225 uses the determined relationship to modify the preparation time associated with the preparation feature corresponding to the ingredient. For example, it takes significantly longer to mash one dozen potatoes than to mash a single potato. By modifying the preparation time based on the quantity an ingredient, the recipe model 220 accounts for variance in preparation times due to preparing more or less of a food item.

In one embodiment, the preparation time estimator 225 combines the preparation times associated with the preparation features as a sum or other linear combination. In an alternative embodiment, the preparation time estimator 225 treats preparation steps differently depending on whether the preparation step contains an explicit time instruction. If the preparation time estimator 225 determines that a preparation step contains an explicit time instruction, then the preparation time estimator 225 adds the explicit time instruction to the total preparation time in lieu of adding contributions to the total preparation time from other preparation features in the preparation step. If the preparation step does not contain an explicit time instruction, then the preparation time estimator 225 adds the preparation times associated with the preparation features of the preparation step to the total preparation time. Hence, the preparation time estimator 225 may add preparation times of preparation features in a recipe's preparation steps subject to conditional logic that may remove some preparation features' combination to the total preparation time.

In one embodiment, the preparation time estimator 225 uses natural language processing to identify discourse cues. Using identified discourse cues, the preparation time estimator 225 modifies the combination of preparation times from steps associated with the discourse cues according to deterministic rules. For example, the discourse cues "while," "meanwhile," and "in another <cooking equipment>" indicate that two or more preparation steps are performed in parallel. Natural language processing may be used to determine which preparation features are associated with a discourse cue. To combine preparation times from preparation steps performed in parallel, the preparation time estimator 225 may omit the preparation times from the preparation step that takes less total time. As another example, the discourse cues "or" and "alternatively" indicate that a preparation step may be performed in different ways. To combine preparation times corresponding to alternative preparation features, the preparation time estimator 225 may use an average of the alternative preparation features or compute a range of total preparation times based on different alternatives in a recipe.

The preparation time estimator 225 may further modify the estimated total preparation time. In one embodiment, the total preparation time is rounded up, rounded down, or rounded to a given increment of time (e.g., to the nearest quarter hour, up to the next multiple of five minutes). By rounding the total preparation time, the preparation time estimator 225 eliminates unwarranted implied precision and increases the readability of the total preparation time to a viewing user. The preparation time estimator 225 may also add a supplemental time to the total preparation time to ensure that an average cook can prepare the recipe's food item in under the stated total preparation time. For example, the preparation time estimator 225 adds a fixed increment of time or adds an increment of time proportional to the total preparation time. In one implementation, the supplemental time is between five percent and thirty percent of the total preparation time.

In one embodiment, the supplemental time is determined dynamically based on an inferred skill of the user requesting a recipe. The preparation time estimator 225 may increase the supplemental time for more skilled cooks and decrease the supplemental time for less skilled cooks. The cooking skill of a user may be retrieved from a profile of the user on the recipe server 120. A user may explicitly indicate cooking skill as part of a user profile, or the recipe server 120 may infer the skill from an average difficulty attribute associated with recipes that a user has rated, commented on, or otherwise interacted with. Hence, the preparation time estimator 225 determines the total preparation time based on preparation times associated with the preparation features of a recipe's preparation steps. The estimated total preparation time may be stored in association with the recipe in the recipe store 205.

Applications of Total Recipe Preparation Time

The recipe browsing interface 230 uses the estimated total preparation time in an interface for browsing and searching for recipes. For example, the browsing interface 230 displays the total preparation time in a summary of a recipe that also includes the recipe's title and a representative image of the recipe. As another example, the browsing interface 230 presents a collection of recipes having total preparation times falling with a particular range. For example, the interface 230 presents "quick and easy recipes" having total preparation times of forty-five minutes or less as well as "savory Sunday meals" having total preparation times between two and four hours. The recipe browsing interface 230 may also display the recipe preparation time in a detailed view of the recipe displaying its ingredients and preparation steps. If a client device 130 requests a recipe, then the recipe server 120 transmits the recipe including its estimated total preparation time to the client device 130 in response.

The recipe search engine 235 may use the estimated total preparation time to screen recipes in response to a request for recipes. In one embodiment, the recipe search engine 235 receives a request for recipes (such as a search query) from a client device 130. The request for recipes (or search query) specifies one or more criteria such as a threshold preparation time or a range of preparation times. The threshold preparation time indicates a minimum or maximum total preparation time for recipes meeting the criteria. The range includes an upper threshold and a lower threshold defining the range. The recipe search engine 235 identifies recipes from the recipe store 205 that have a total preparation time within the threshold preparation time or within the range of preparation times. Recipes determined to have total preparation times within the specified threshold preparation time (or range of preparation times) are transmitted to the client device 130. For example, recipes meeting the criteria are displayed in the recipe browsing interface 230. Other example criteria in the request for recipes could include ingredients in a recipe, dietary restrictions a recipe complies with, meals, cuisines, occasions, or recipe titles. Hence, the recipe search engine 235 provides more relevant responses to user requests for recipes.

The recipe recommendation engine 240 may use the estimated total preparation time to select recipes that are more relevant to a user. In one embodiment, the recipe server 120 stores user preferences including preferences for total preparation times of recipes. The user preferences may include deterministic rules (e.g., no recipes under ten minutes, no recipes over one hour) or may represent tendencies of a user. The recipe recommendation engine 240 selects a subset of recipes to recommend to the user based on preparation times of those recipes and user preferences of the user. For example, a user's preferences indicate that the user is partial towards recipes between one and two hours, so the recipe recommendation engine 240 is more likely to select recipes for the user with total preparation times falling in this range.

The recipe recommendation engine 240 may retrieve user preferences (e.g. through the recipe browsing interface 230) or may infer user preferences. For example, the recipe browsing interface 230 includes feedback mechanisms (e.g., ratings) for a user to express an opinion towards a recipe. In this example, the recipe recommendation engine 240 modifies a user's inferred preferences in concordance with ratings of recipes and total preparation times for rated recipes. Hence, the recipe recommendation engine 240 selects recipes for presentation to a user based in part on total preparation times of selected recipes and user preferences about total preparation times.

Recipe Preparation Time Inference

Figure 3:
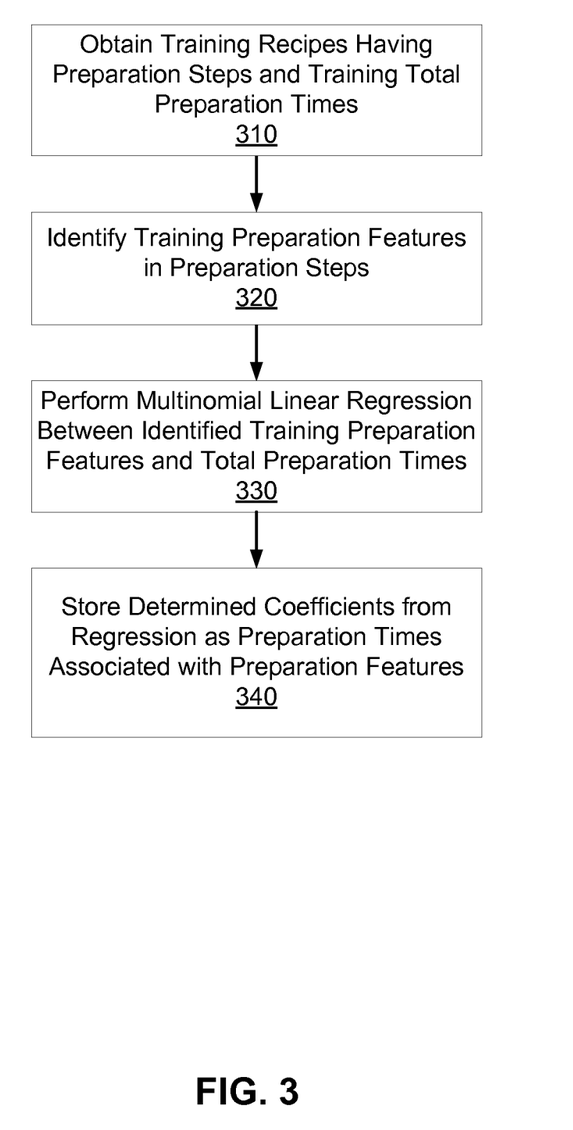
FIG. 3 is a flowchart illustrating a method for training a recipe model to determine preparation times associated with preparation features of a recipe, in accordance with an embodiment.

FIG. 3 is a flowchart illustrating a method for training a recipe model to determine preparation times associated with preparation features of a recipe, in accordance with an embodiment. The recipe server 120 obtains 310 training recipes having preparation steps and training total preparation times. For example, the recipes are retrieved from the recipe source 110 or from the recipe store 205.

The preparation feature identifier 215 identifies 320 training preparation features in the preparation steps of the recipe (or in other components of the recipe such as the ingredients or the title). For example, the preparation feature identifier 215 identifies 320 preparation features by matching text of the preparation steps to nodes of a food knowledge graph.

The preparation time model 220 performs 330 a linear regression between the identified training preparation features and the training total preparation times of the recipe. The determined coefficients of the linear regression are preparation times associated with respective training preparation features. The preparation time model 220 may use some other statistical or machine learning technique to determine preparation times that estimate the training total preparation times of a recipe from the training preparation steps. Additionally, the preparation time model 220 may include additional deterministic logic for selecting a subset of training preparation features to use in the regression or other model.

The preparation time model 220 then optionally stores 340 the determined preparation times associated with preparation features for later use by the preparation time estimator 225.

Determining preparation times may be performed as a batch process (e.g., periodically), or preparation times may be updated based on preparation times determined from previously unconsidered training recipes. For example, the preparation time model 220 updates the preparation times using a weighted average between previously determined preparation times and preparation times determined for the previously unconsidered training recipes.

Figure 4:
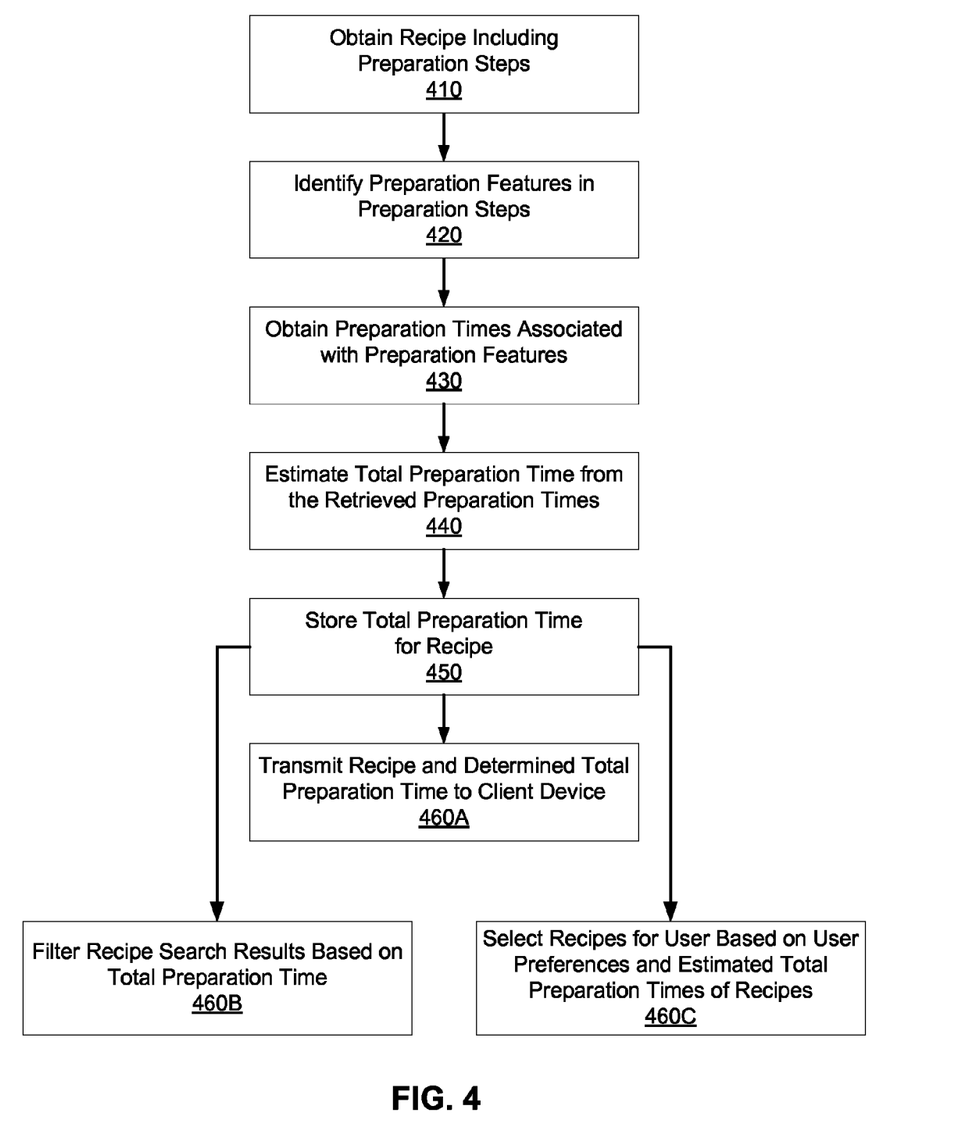
FIG. 4 is a flowchart illustrating a method for estimating a total preparation time of a recipe, in accordance with an embodiment.

FIG. 4 is a flowchart illustrating a method for estimating a total preparation time of a recipe, in accordance with an embodiment. The recipe server 120 obtains 410 recipes (e.g., from a recipe source 110, from the recipe store 205) including preparation steps describing how to prepare a food item described by the recipe.

From the obtained recipe, the preparation feature identifier 215 identifies 420 preparation features in the preparation steps. These preparation features represent portions of the preparation steps that are indicative of time to prepare the recipe. For example, the preparation feature identifier 215 identifies 420 preparation features by matching text of the preparation steps to nodes of a food knowledge graph. Other example preparation features correspond to text in a preparation step or an explicit time in a preparation step.

The preparation time estimator 225 obtains 430 preparation times associated with the identified preparation features (e.g., retrieving stored preparation times, determining preparation times). For example, the preparation time model 420 determines the preparation times as described with respect to FIG. 3.

By combining the preparation times associated with the preparation features, the preparation time estimator 225 estimates 440 the total preparation time of the obtained recipe. For example, the preparation time estimator 225 sums the preparation times associated with the preparation features. In one embodiment, the preparation time estimator selects a subset of preparation times based on deterministic logic and then combines the selected subset to estimate 440 the total preparation time. For example, if a preparation feature containing an explicit time is identified from a preparation step, then other preparation features from that preparation step are omitted from the sum.

The preparation time estimator 225 then optionally stores 450 the estimated total preparation time of the recipe (e.g., in the recipe store 205 in association with the recipe).

The recipe server 120 may use the estimated total preparation time for various other functions. For instance, the recipe server 120 includes the total preparation time of a recipe in a recipe browsing interface 230. When a client device 130 requests to view a recipe, the recipe server 120 transmits 460A the recipe including the total preparation time to the client device 130.

The recipe server 120 may also filter 460B search results (or other requests for recipes) based on the total preparation time. For example, the recipe server 120 receives a request from a client device 130 for recipes having a total preparation time within a threshold or range. The recipe search engine 235 determines whether recipes have total preparation times within the threshold or range and transmits those recipes that do fit the total preparation time criteria to the client device 130.

The recipe recommendation engine 240 may select 460C recipes for a user based at least in part on user preferences of the user and total preparation times of the recipes. For example, the user preferences include a binary filter based on a total preparation time criterion, or the user preferences indicate a relationship between the total preparation time and the user's reported enjoyment of recipes (e.g., as indicated through a feedback mechanism in the recipe browsing interface 230). Thus, the recipe server 120 may use the total preparation time in one or more different contexts.

Example Recipe

Figure 5:
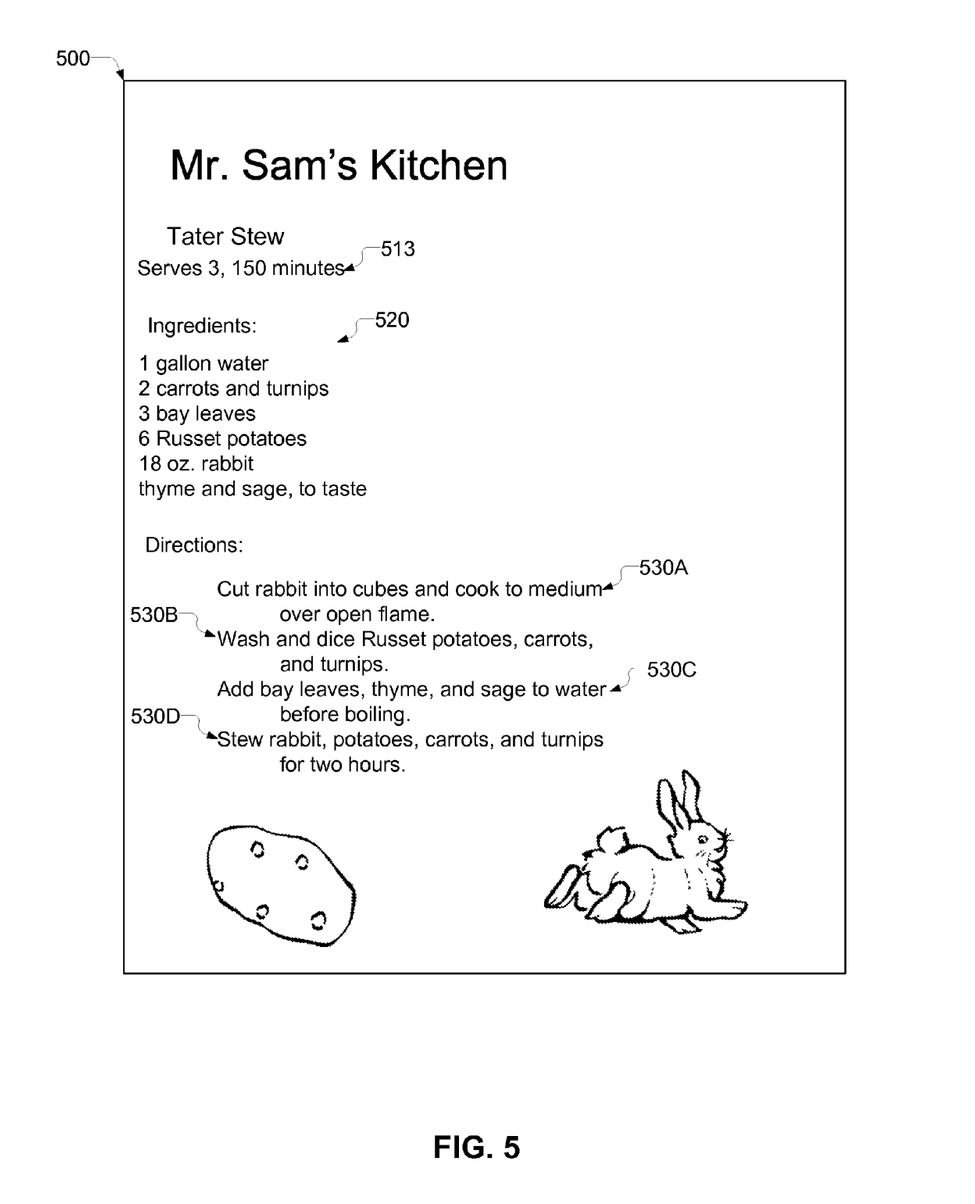
FIG. 5 illustrates an example recipe from a recipe source, in accordance with an embodiment.

FIG. 5 illustrates an example recipe 500 from a recipe source 110 with example recipe component classifications, in accordance with an embodiment. The recipe includes a total preparation time 513, recipe ingredients 520, and preparation steps 530A-D (referred to generally as "preparation steps 530"). The total preparation time 513 may be a total recipe preparation time 513 obtained from a recipe source 110 (if the recipe source includes a total preparation time) or an estimated total preparation time determined by the preparation time estimator 225.

The preparation steps 530 describe how to prepare the food item—in this case "Tater Stew." In the preparation step 530A, the cooking technique identifier 217 recognizes "cutting" as the cooking technique. The preparation feature identifier 215 generates preparation features corresponding to this technique and to the cooking equipment and creates a preparation feature corresponding to the cooking equipment "open flame." Additionally, the preparation feature identifier 215 may generate a preparation feature corresponding to the text "cook to medium." For the preparation step 530B, the preparation feature identifier 215 generates preparation features corresponding to the cooking techniques "washing" and "dicing." The preparation feature identifier 215 may also generate preparation features corresponding to the text "dice . . . Russet potatoes," "dice . . . carrots," and "dice . . . turnips." These features are each associated with separation preparation times. For the preparation step 530C, the preparation feature identifier 215 generates preparation features corresponding to the cooking technique "adding" rather than the cooking technique "boiling" because the cooking technique identifier 217 recognizes "add" as the verb of the sentence's main clause. The preparation time associated with "adding" may be relatively low compared to some preparation steps, but it is still non-negligible because steps to "add" ingredients include an implicit instruction to gather and measure the ingredients to be added. Lastly, the preparation feature identifier 215 generates features for preparation step 530D corresponding to the cooking technique "stewing" and the explicit time instruction "two hours." When the preparation times associated with the identified features are combined to estimate to the total preparation time 513, the preparation time estimator 225 may omit the preparation time associated with "stewing" because preparation step 530D includes an explicit time instruction.

Knowledge Graph

Figure 6A:
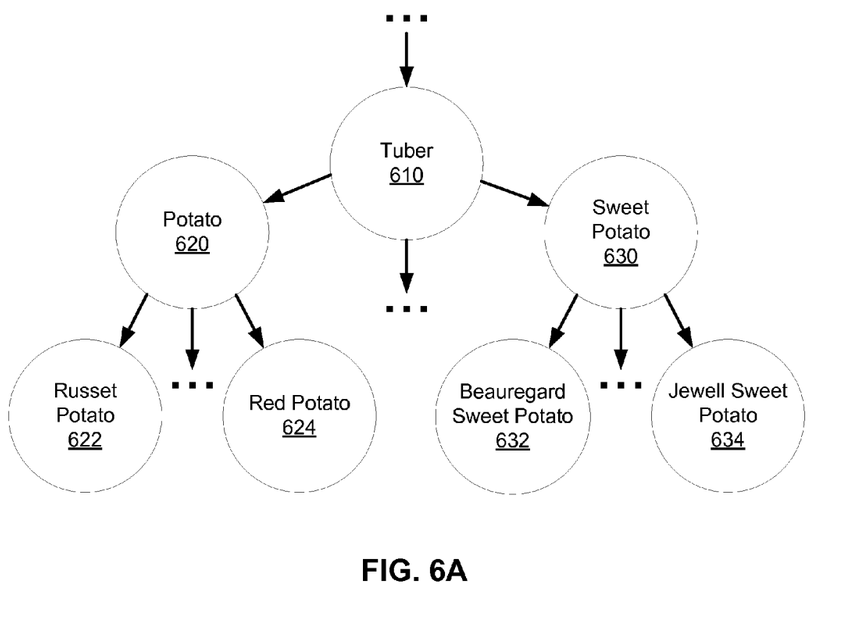
FIGS. 6A and 6B are conceptual diagrams illustrating example sections of the knowledge graph, in accordance with an embodiment.
Figure 6B:
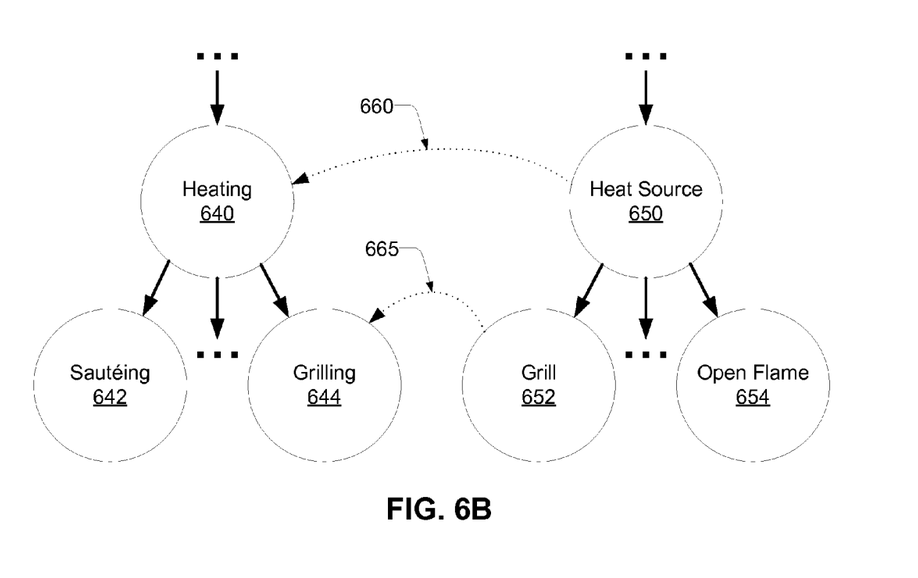

FIGS. 6A and 6B are conceptual diagrams illustrating example sections of the knowledge graph, in accordance with an embodiment. The example section of the knowledge graph illustrated in FIG. 6A includes nodes representing ingredients such as a Russet potato 622, a red potato 624, a Beauregard sweet potato 632, and a Jewell sweet potato 634. The example section also includes abstractions of ingredients including a potato 620, a sweet potato 630, and a tuber 610. The directed edges indicate relationships among the nodes of the illustrated section. In this case, an edge from a first node to a second node indicates that the second node represents an instance of an abstraction represented by the first node. For example, a Russet potato 622 and a red potato 624 are instances of a potato 620, and the potato 620 and the sweet potato 630 are instances of the tuber 610. The ellipses indicate that the illustrated section is an excerpt of an example knowledge graph from the knowledge graph store 210. For instance, the tuber 610 is an instance of the abstraction "root vegetable," and there are additional types of potatoes 610, sweet potatoes 620, and tubers 630. Hence, the knowledge graph organizes food information.

The example sections of the knowledge graph illustrated in FIG. 6B include nodes representing cooking techniques and cooking equipment, respectively. Similar to the section of the graph representing ingredients, a directed edge from a first node to a second node indicates that the second node represents an instance of an abstraction represented by the first node. Thus, the cooking techniques sautéing 642 and grilling 644 are instances of cooking 640, which is a cooking technique abstraction. The cooking equipment grill 652 and open flame 654 are instances of the cooking equipment abstraction heat source 650. The directed edges 660 and 665 from nodes representing cooking equipment to nodes representing cooking techniques indicate that the cooking equipment is used to perform the cooking technique. For example, the directed edge 660 indicates that a heat source 650 is used for heating 640, and the directed edge 665 indicates that a grill 652 is used for grilling 644.

The preparation time estimator 225 may use the food knowledge graph in estimating a total preparation time. When there is not a preparation time associated with a preparation feature, the preparation time estimator 225 may use the food knowledge graph to find a preparation time associated with a similar preparation feature. This similar preparation feature may have an abstraction of a cooking technique, cooking equipment, or an ingredient in the preparation feature. For example, if the preparation feature corresponding to the text "dice . . . Russet potatoes" does not have an associated preparation time, the preparation time estimator 225 may substitute a preparation time associated with the preparation feature corresponding to the text "dice . . . potatoes" because Russet potatoes 622 are an instance of potatoes 620 in the food knowledge graph. As another example, if there is no preparation time associated with a preparation feature corresponding to the cooking equipment open flame 654, then the preparation time estimator 225 uses a preparation time associated with the cooking equipment heat source 650.

Computer System

Figure 7:
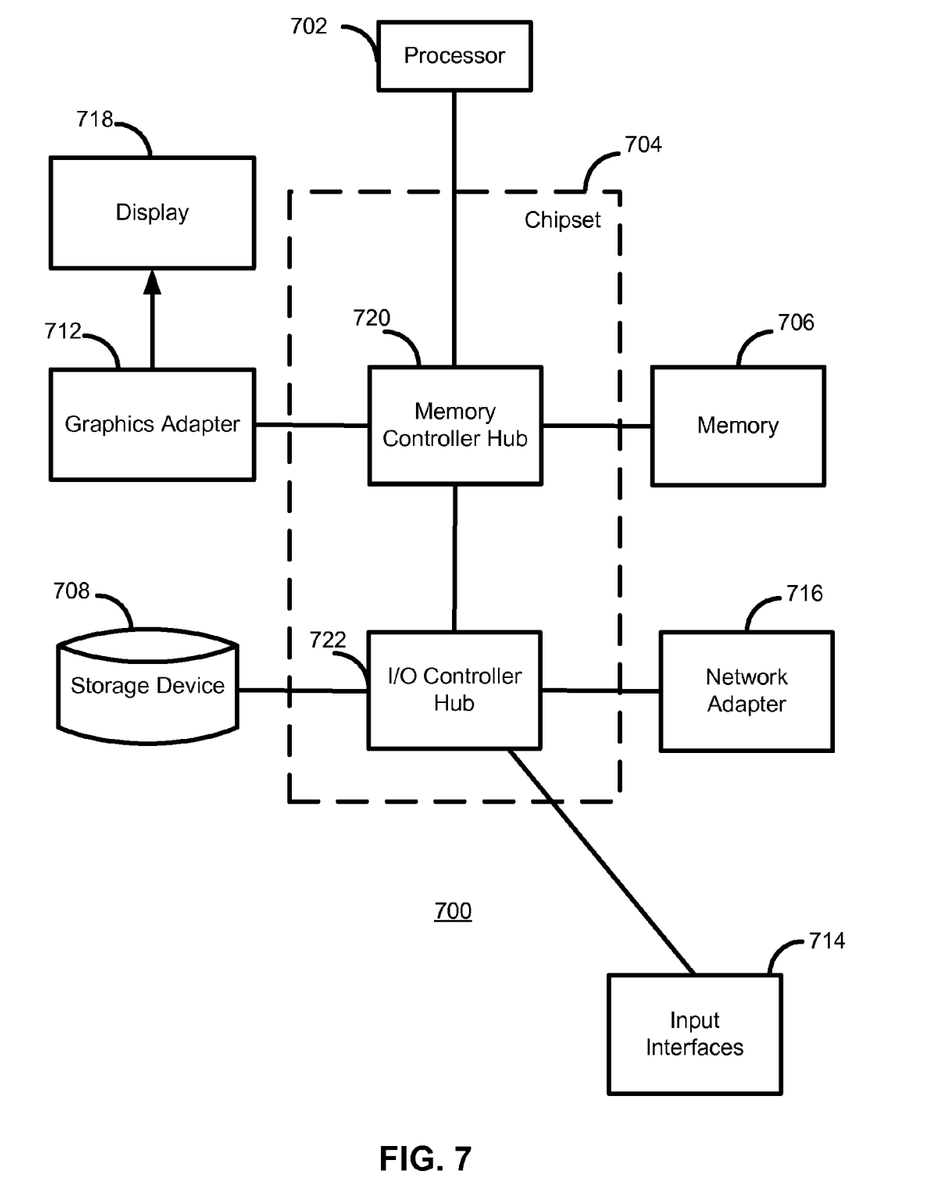
FIG. 7 is a block diagram illustrating an example computer for implementing the entities such as the recipe server shown in FIG. 2, in accordance with an embodiment.

FIG. 7 is a block diagram illustrating an example computer for implementing the entities such as the recipe server 120 shown in FIG. 1, in accordance with an embodiment. The computer 700 includes at least one processor 702 coupled to a chipset 704. The chipset 704 includes a memory controller hub 720 and an input/output (I/O) controller hub 722. A memory 706 and a graphics adapter 712 are coupled to the memory controller hub 720, and a display 718 is coupled to the graphics adapter 712. A storage device 708, input interfaces 714, and network adapter 716 are coupled to the I/O controller hub 722. Other embodiments of the computer 700 have different architectures.

The storage device 708 is a non-transitory computer-readable storage medium such as a hard drive, compact disk read-only memory (CD-ROM), DVD, or a solid-state memory device. The memory 706 holds instructions and data used by the processor 702. The input interfaces 714 may include a touch-screen interface, a mouse, track ball, or other type of pointing device, a keyboard, a scanner or other conventional digitizer, or some combination thereof, and is used to input data into the computer 700. The graphics adapter 712 displays images and other information on the display 718. The network adapter 716 couples the computer 700 to one or more computer networks.

The computer 700 is adapted to execute computer program modules (e.g., the preparation feature identifier 215, the cooking technique identifier 217, the preparation time model 220). As used herein, the term "module" refers to computer program logic used to provide the specified functionality. Thus, a module may be implemented in hardware, firmware, and/or software. In one embodiment, program modules are stored on the storage device 708, loaded into the memory 706, and executed by the processor 702.

The type of computer 700 used by the entities of the environment 100 can vary depending upon the embodiment. For example, the recipe source 110 or recipe server 120 may include multiple computers 700 communicating with each other through the network 140 to provide the functionality described herein. Such computers 700 may lack some of the components described above, such as graphics adapters 712 and displays 718. As another example, the client device 130 is implemented on a mobile device, laptop, or tablet containing at least some of the components of the computer 700.

Additional Considerations

Some portions of the above description describe the embodiments in terms of algorithmic processes or operations. These algorithmic descriptions and representations are commonly used by those skilled in the data processing arts to convey the substance of their work effectively to others skilled in the art. These operations, while described functionally, computationally, or logically, are understood to be implemented by computer programs comprising instructions for execution by a processor or equivalent electrical circuits, microcode, or the like. Furthermore, it has also proven convenient at times, to refer to these arrangements of functional operations as modules, without loss of generality. The modules described herein represent an implementation of one embodiment, but various other embodiments may include additional, fewer, or different modules to implement the methods, systems, or non-transitory, computer-readable media delineated in the accompanying claims. The described operations and their associated modules may be embodied in software, firmware, hardware, or any combinations thereof.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or"

refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the disclosure. This description should be read to include one or at least one and the singular also includes the plural unless it is obvious that it is meant otherwise.

Upon reading this disclosure, those of skill in the art will appreciate still additional alternative structural and functional designs. Thus, while particular embodiments and applications have been illustrated and described, it is to be understood that the described subject matter is not limited to the precise construction and components disclosed herein and that various modifications, changes and variations which will be apparent to those skilled in the art may be made in the arrangement, operation and details disclosed herein.

What is claimed is:

1. A computer-implemented method for inferring a total preparation time of a recipe, the method comprising:
    obtaining a recipe comprising a plurality of preparation steps describing how to prepare a food item described by the recipe;
    identifying, by a processor, preparation features in the preparation steps, the preparation features representing portions of the preparation steps indicative of time to prepare the recipe;
    obtaining preparation times associated with the preparation features, obtaining the preparation times comprising:
        identifying training preparation features in training recipes having known total preparation times;
        predicting the preparation times of the training preparation features by training a preparation time model using the known total preparation times of the training recipes; and
        determining the preparation times associated with the preparation features responsive to the predicted preparation times of the training preparation features;
    estimating the total preparation time of the recipe by combining the preparation times associated with the preparation features;
    storing the total preparation time of the recipe;
    receiving, from a client device, a request for recipes, the request including a threshold preparation time;
    determining whether the total preparation time of the recipe is within the threshold preparation time; and
    transmitting the recipe to the client device in response to determining that the total preparation time of the recipe is within the threshold preparation time.

2. The method of claim 1, wherein transmitting the recipe comprises:
    transmitting the recipe and the estimated total preparation time to the client device in response to the request for recipes from the client device.

3. The method of claim 1, wherein a plurality of total preparation times for a plurality of recipes are stored, the method further comprising:
    selecting a subset of the plurality of recipes to recommend to the user based at least in part on the plurality of total preparation times and user preferences of the user.

4. The method of claim 1, wherein identifying preparation features in the preparation steps comprises:
    identifying preparation features by matching text of the preparation steps to nodes of a food knowledge graph, the nodes representing food terms comprising at least one of: equipment to prepare food items, techniques to prepare food items, and ingredients in food items.

5. The method of claim 1, wherein obtaining the preparation times further comprises:
    retrieving the preparation times determined by training the preparation time model.

6. The method of claim 1, predicting the preparation times comprises:
    using a linear regression between the training preparation features and the known total preparation times of the training recipes.

7. The method of claim 1, wherein estimating the total preparation time of the recipe comprises:
    for each preparation step of the preparation steps:
        determining whether the preparation step contains an explicit time instruction; and
        adding, to the total preparation time, an explicit time duration contained in the explicit time instruction in response to determining that the preparation step contains the explicit time instruction.

8. The method of claim 1, further comprising:
    adding supplemental time to the total preparation time prior to storing the total preparation time.

9. The method of claim 8, wherein the supplemental time is between five percent of the total preparation time and thirty percent of the total preparation time.

10. A non-transitory computer-readable storage medium comprising instructions for inferring a total preparation time of a recipe, the instructions when executed by a processor causing the processor to:
    obtain a recipe comprising a plurality of preparation steps describing how to prepare a food item described by the recipe;
    identify preparation features in the preparation steps, the preparation features representing portions of the preparation steps indicative of time to prepare the recipe;
    obtain preparation times associated with the preparation features, obtaining the preparation times comprising:
        identifying training preparation features in training recipes having known total preparation times;
        predicting the preparation times of the training preparation features by training a preparation time model using the known total preparation times of the training recipes; and
        determining the preparation times associated with the preparation features responsive to the predicted preparation times of the training preparation features;
    estimate the total preparation time of the recipe by combining the preparation times associated with the preparation features;
    store the total preparation time of the recipe;
    receive, from a client device, a request for recipes, the request including a threshold preparation time;
    determine whether the total preparation time of the recipe is within the threshold preparation time; and
    transmit the recipe to the client device in response to determining that the total preparation time of the recipe is within the threshold preparation time.

11. The computer-readable storage medium of claim 10, wherein transmitting the recipe comprises:

transmitting the recipe and the estimated total preparation time to the client device in response to the request for recipes from the client device.

12. The computer-readable storage medium of claim 10, wherein a plurality of total preparation times for a plurality of recipes are stored, the medium further comprising instructions that when executed by the processor cause the processor to:

select a subset of the plurality of recipes to recommend to the user based at least in part on the plurality of total preparation times and user preferences of the user.

13. The computer-readable storage medium of claim 10, wherein the instructions to identify the preparation features in the preparation steps comprise instructions that when executed by the processor cause the processor to:

identify preparation features by matching text of the preparation steps to nodes of a food knowledge graph, the nodes representing food terms comprising at least one of: equipment to prepare food items, techniques to prepare food items, and ingredients in food items.

14. A system for inferring a total preparation time of a recipe, the system comprising:

a processor;

a non-transitory computer-readable storage medium comprising instructions that when executed by the processor cause the processor to:

obtain a recipe comprising a plurality of preparation steps describing how to prepare a food item described by the recipe;

identify preparation features in the preparation steps, the preparation features representing portions of the preparation steps indicative of time to prepare the recipe;

obtain preparation times associated with the preparation features, obtaining the preparation times comprising:

identifying training preparation features in training recipes having known total preparation times;

predicting the preparation times of the training preparation features by training a preparation time model using the known total preparation times of the training recipes; and determining the preparation times associated with the preparation features responsive to the predicted preparation times of the training preparation features;

estimate the total preparation time of the recipe by combining the preparation times associated with the preparation features;

store the total preparation time for the recipe;

receive, from a client device, a request for recipes, the request including a threshold preparation time;

determine whether the total preparation time of the recipe is within the threshold preparation time; and transmit the recipe to the client device in response to determining that the total preparation time of the recipe is within the threshold preparation time.

15. The system of claim 14, wherein transmitting the recipe comprises:

transmitting the recipe and the estimated total preparation time to the client device in response to the request for recipes from the client device.

\* \* \* \* \*